(12) United States Patent
Laredo et al.

(10) Patent No.: US 8,574,292 B2
(45) Date of Patent: *Nov. 5, 2013

(54) OPHTHALMIC AND OTORHINOLARYNGOLOGICAL DEVICE MATERIALS CONTAINING AN ALKYLPHENOL ETHOXYLATE

(75) Inventors: Water R. Laredo, Fort Worth, TX (US); Douglas C. Schlueter, Azle, TX (US)

(73) Assignee: Novartis AG, Basel (CH)

( * ) Notice: Subject to any disclaimer, the term of this patent is extended or adjusted under 35 U.S.C. 154(b) by 635 days.

This patent is subject to a terminal disclaimer.

(21) Appl. No.: 12/243,046

(22) Filed: Oct. 1, 2008

(65) Prior Publication Data

US 2009/0088493 A1  Apr. 2, 2009

Related U.S. Application Data

(60) Provisional application No. 60/976,980, filed on Oct. 2, 2007.

(51) Int. Cl.
- *A61F 2/16* (2006.01)
- *A61F 2/14* (2006.01)
- *C08F 20/10* (2006.01)
- *C08F 20/18* (2006.01)
- *C08F 118/02* (2006.01)
- *C08F 18/02* (2006.01)
- *C08F 220/68* (2006.01)
- *C08F 22/10* (2006.01)
- *C08F 18/16* (2006.01)
- *C08F 220/10* (2006.01)
- *C08F 220/12* (2006.01)

(52) U.S. Cl.
USPC ........ 623/6.11; 623/5.11; 623/5.12; 526/318; 526/319; 526/320; 526/321; 526/326; 526/327; 526/328.5; 526/329.6

(58) Field of Classification Search
USPC .......... 523/106; 526/319, 318, 320, 321, 327, 526/326, 329.6, 328.5; 623/6.11, 5.11, 5.12
See application file for complete search history.

(56) References Cited

U.S. PATENT DOCUMENTS

| | | |
|---|---|---|
| 4,032,599 A | 6/1977 | Cordrey et al. |
| 5,070,169 A | 12/1991 | Robertson et al. |
| 5,290,892 A | 3/1994 | Namdaran et al. |
| 5,331,073 A | 7/1994 | Weinschenk, III et al. |
| 5,334,681 A | 8/1994 | Mueller et al. |
| 5,470,932 A | 11/1995 | Jinkerson |
| 5,693,095 A | 12/1997 | Freeman et al. |
| 5,944,853 A * | 8/1999 | Molock et al. ............... 8/506 |
| 6,353,069 B1 | 3/2002 | Freeman et al. |
| 6,528,602 B1 | 3/2003 | Freeman et al. |
| 6,653,422 B2 | 11/2003 | Freeman et al. |
| 2004/0056371 A1* | 3/2004 | Liao et al. .................. 264/2.5 |
| 2004/0131849 A1* | 7/2004 | Wires ......................... 428/375 |
| 2005/0085585 A1 | 4/2005 | Quinn et al. |
| 2006/0134169 A1 | 6/2006 | Linhardt et al. |
| 2006/0275342 A1 | 12/2006 | Linhardt et al. |

FOREIGN PATENT DOCUMENTS

| | | |
|---|---|---|
| EP | 329981 A1 * | 8/1989 |
| EP | 0395583 B1 | 9/1997 |
| EP | 1818690 A1 | 8/2007 |
| JP | 0733841 | 2/1995 |
| JP | 07033841 A * | 2/1995 |
| JP | 2005126622 A * | 5/2005 |
| WO | WO9724382 A1 | 7/1997 |
| WO | WO2006068705 A1 | 6/2006 |
| WO | WO2006130402 A2 | 12/2006 |
| WO | WO2006138188 A1 | 12/2006 |
| WO | WO2006138213 A1 | 12/2006 |

OTHER PUBLICATIONS

Machine translation of JP 07033841 A; Nakayama et al; Feb. 1995.*
Abstract in English; JP 07033841 A; Nakayama et al; Feb. 1995.*
Yamamoto et al; Machine translation of JP 2005126622 A; May 2005.*
Aronix; Data for M-113; Sep. 2009.*

* cited by examiner

*Primary Examiner* — Karuna P Reddy
(74) *Attorney, Agent, or Firm* — Patrick M. Ryan

(57) ABSTRACT

Disclosed are soft, high refractive index, acrylic device materials. The materials contain a functionalized alkylphenol ethoxylate to reduce glistenings.

12 Claims, No Drawings

OPHTHALMIC AND OTORHINOLARYNGOLOGICAL DEVICE MATERIALS CONTAINING AN ALKYLPHENOL ETHOXYLATE

This application claims priority to U.S. Provisional Application, U.S. Ser. No. 60/976,980 filed Oct. 2, 2007.

FIELD OF THE INVENTION

This invention is directed to improved ophthalmic and otorhinolaryngological device materials. In particular, this invention relates to soft, high refractive index acrylic device materials that have improved glistening resistance.

BACKGROUND OF THE INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Conventional silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a high refractive index and unfold more slowly or controllably than conventional silicone materials.

U.S. Pat. No. 5,290,892 discloses high refractive index, acrylic materials suitable for use as an intraocular lens ("IOL") material. These acrylic materials contain, as principal components, two aryl acrylic monomers. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable, high refractive index ophthalmic lens materials containing at least about 90 wt. % of only two principal components: one aryl acrylic hydrophobic monomer and one hydrophilic monomer. The aryl acrylic hydrophobic monomer has the formula

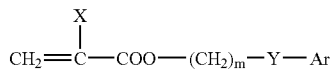

wherein: X is H or $CH_3$;
m is 0-6;
Y is nothing, O, S, or NR, wherein R is H, $CH_3$, $C_nH_{2n+1}$ (n=1-10), iso-$OC_3H_7$, $C_6H_5$, or $CH_2C_6H_5$; and Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

The lens materials described in the '095 Patent preferably have a glass-transition temperature ("$T_g$") between about −20 and +25° C.

Flexible intraocular lenses may be folded and inserted through a small incision. In general, a softer material may be deformed to a greater extent so that it can be inserted through an increasingly smaller incision. Soft acrylic or methacrylic materials typically do not have an appropriate combination of strength, flexibility and non-tacky surface properties to permit IOLs to be inserted through an incision as small as that required for silicone IOLs.

Polyethylene glycol (PEG) dimethacrylates are known to improve glistening resistance of hydrophobic acrylic formulations. See, for example, U.S. Pat. Nos. 5,693,095; 6,528, 602; 6,653,422; and 6,353,069. Both the concentration and molecular weight of PEG dimethacrylates have an impact on glistening performance. Generally, use of higher molecular weight PEG dimethacrylates (1000 MW) yield copolymers with improved glistening performance at low PEG concentrations (10-15 wt %), as compared to lower molecular weight PEG dimethacrylates (<1000 MW). However, low PEG dimethacrylate concentrations are desirable to maintain a high refractive index copolymer. Addition of PEG dimethacrylates also tends to decrease the modulus and tensile strength of the resulting copolymer. Also, higher molecular weight PEG dimethacrylates are generally not miscible with hydrophobic acrylic monomers.

SUMMARY OF THE INVENTION

Improved soft, foldable acrylic device materials which are particularly suited for use as IOLs, but which are also useful as other ophthalmic or otorhinolaryngological devices, such as contact lenses, keratoprostheses, corneal rings or inlays, otological ventilation tubes and nasal implants, have been discovered. These polymeric materials comprise an alkylphenol ethoxylate monomer.

Among other factors, the present invention is based on the finding that use of alkylphenol ethoxylate monomers in acrylic intraocular lens formulations reduces or eliminates temperature-induced glistening formation in hydrophobic acrylic copolymers. The subject monomers allow synthesis of glistening resistant, low equilibrium water content, high refractive index IOLs.

DETAILED DESCRIPTION OF THE INVENTION

Unless indicated otherwise, all component amounts are presented on a % (w/w) basis ("wt. %").

The device materials of the present invention are copolymers comprising a) a monofunctional acrylate or methacrylate monomer [1], b) a difunctional acrylate or methacrylate cross-linker [2], and c) a functionalized alkylphenol ethoxylate [3]. The device materials may contain more than one monomer [1], more than one monomer [2], and more than one monomer [3]. Unless indicated otherwise, references to each ingredient are intended to encompass multiple monomers of the same formula and references to amounts are intended to refer to the total amount of all monomers of each formula.

$$[1]$$

wherein
B=$O(CH_2)_n$, $NH(CH_2)_n$, or $NCH_3(CH_2)_n$;
$R^1$=H, $CH_3$, $CH_2CH_3$, or $CH_2OH$;
n=0-12;
A=$C_6H_5$ or $O(CH_2)_mC_6H_5$, where the $C_6H_5$ group is optionally substituted with —$(CH_2)_nH$, —$O(CH_2)_nH$, —$CH(CH_3)_2$, —$C_6H_5$, —$OC_6H_5$, —$CH_2C_6H_5$, F, Cl, Br, or I; and
m=0-22;

$$[2]$$

wherein
$R^2$, $R^3$ independently=H, $CH_3$, $CH_2CH_3$, or $CH_2OH$;
W, W' independently=$O(CH_2)_d$, $NH(CH_2)_d$, $NCH_3(CH_2)_d$, $O(CH_2)_dC_6H_4$, $O(CH_2CH_2O)_dCH_2$, $O(CH_2CH_2CH_2O)_dCH_2$, $O(CH_2CH_2CH_2CH_2O)_dCH_2$, or nothing;
J=$(CH_2)_a$, $O(CH_2CH_2O)_b$, O, or nothing, provided that if W and W'=nothing, then J≠ nothing;
d=0-12;
a=1-12;
b=1-24;

$$[3]$$

wherein:
T=$C_8H_{17}$ or $C_9H_{19}$;
e=1-100;

$$Y = -\underset{R^4}{\overset{}{C}}=CH_2 \quad \text{or} \quad -\underset{}{\overset{H}{N}}-R^5;$$

$R^4$=H, $CH_3$, $CH_2CH_3$, $CH_2OH$; and $R^5$ = $CH_2CH_2OC(=O)C(CH_3)=CH_2$ or $C(CH_3)_2$—⟨phenyl⟩—$C(CH_3)=CH_2$.

Preferred monomers of formula [1] are those wherein:
B=$O(CH_2)_n$;
$R^1$=H or $CH_3$;
n=1-4; and
A=$C_6H_5$.

Preferred monomers of formula [2] are those wherein:
$R^2$, $R^3$ independently=H or $CH_3$;
W, W' independently=$O(CH_2)_d$, $O(CH_2)_dC_6H_4$, or nothing;
J=$O(CH_2CH_2O)_b$, or nothing, provided that if W and W'=nothing, then J≠nothing;
d=0-6; and
b=1-10.

Preferred monomers of formula [3] are those wherein:
e=8-50;

$$Y = -\underset{R^4}{\overset{}{C}}=CH_2; \quad \text{and}$$

$R^4$=H or $CH_3$.

Most preferred monomers of formulas [3] are those wherein
T=2,4,4-trimethylpentan-2-yl alkyl or 3-ethyl-4-methylhexan-2-yl alkyl;
e=15-40;

$$Y = -\underset{R^4}{\overset{}{C}}=CH_2; \quad \text{and}$$

$R^4$=H or $CH_3$.

Representative monomers of formula [3] include:

$C_9H_{19}$—⟨phenyl⟩—$(OCH_2CH_2)_x$—O—C(=O)—C(CH_3)=CH_2;

$C_9H_{19}$—⟨phenyl⟩—$(OCH_2CH_2)_x$—O—C(=O)—CH=CH_2;

$C_9H_{19}$—⟨phenyl⟩—$(OCH_2CH_2)_x$—O—C(=O)—NH—CH_2CH_2—O—C(=O)—C(CH_3)=CH_2; and $C_9H_{19}$—⟨phenyl⟩—$(OCH_2CH_2)_x$—O—C(=O)—NH—C(CH_3)_2—⟨phenyl⟩—C(CH_3)=CH_2.

Monomers of formula [1] are known and can be made by known methods. See, for example, U.S. Pat. Nos. 5,331,073 and 5,290,892. Many monomers of formula [1] are commercially available from a variety of sources. Preferred monomers of formula [1] include benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy)ethyl methacrylate; 2-benzyloxyethyl methacrylate; 2-(2-(benzyloxy)ethoxy)ethyl methacrylate; and 3-benzyloxypropyl methacrylate; and their corresponding acrylates.

Monomers of formula [2] are known and can be made by known methods, and are commercially available. Preferred monomers of formula [2] include ethylene glycol dimethacrylate ("EGDMA"); diethylene glycol dimethacrylate; triethylene glycol dimethacrylate; 1,6-hexanediol dimethacrylate; 1,4-butanediol dimethacrylate; 1,4-benzenedimethanol dimethacrylate; and their corresponding acrylates. Most preferred is 1,4-butanediol diacrylate.

Monomers of formula [3] can be made by known methods. For example, such monomers may be made by esterification reactions involving, for example, the alkylphenol ethoxylate alcohol and suitable carboxylic acids, acyl halides, or carboxylic acid anhydrides. For example, the alkylphenol ethoxylate can be heated with a carboxylic acid or carboxylic acid alkyl ester in the presence of a catalyst to form the desired ester, with water or low boiling alcohol as a byproduct which can be removed to drive the reaction to completion. The alkylphenol ethoxylate can also be treated with an acyl halide in the presence of a base such as triethylamine which serves as a hydrohalide acceptor. The alkylphenol ethoxylate can also be treated with a carboxylic acid anhydride in the presence of a base such as triethylamine or pyridine which catalyzes the reaction and neutralizes the acid formed.

The copolymeric materials of the present invention contain a total amount of monomer [1] from 75 to 97%, preferably from 80 to 95%, and most preferably from 80-93%. The difunctional cross-linker [2] concentration is generally present in an amount from 0.5-3%, and preferably 1-2%.

The materials of the present invention have at least one monomer [3]. The total amount of monomer [3] depends on the desired physical properties for the device materials. The copolymeric materials of the present invention contain a total of at least 1% and can contain as much as 20% of monomer [3]. Preferably, the copolymeric device materials will contain from 1 to 15% of monomer [3]. Most preferably, the device materials will contain from 1 to 10% of monomer [3].

The copolymeric device material of the present invention optionally contains one or more ingredients selected from the group consisting of a polymerizable UV absorber and a polymerizable colorant. Preferably, the device material of the present invention contains no other ingredients besides the monomers of formulas [1] and [2], the monomer [3], and the optional polymerizable UV absorbers and colorants.

The device material of the present invention optionally contains reactive UV absorbers or reactive colorants. Many reactive UV absorbers are known. A preferred reactive UV absorber is 2-(2'-hydroxy-3'-methallyl-5'-methylphenyl)benzotriazole, commercially available as o-Methallyl Tinuvin P ("oMTP") from Polysciences, Inc., Warrington, Pa. UV absorbers are typically present in an amount from about 0.1-5%. Suitable reactive blue-light absorbing compounds include those described in U.S. Pat. No. 5,470,932. Blue-light absorbers are typically present in an amount from about 0.01-0.5%. When used to make IOLs, the device materials of the present invention preferably contain both a reactive UV absorber and a reactive colorant.

In order to form the device material of the present invention, the chosen ingredients [1], [2], and [3], along with any of the optional ingredients, are combined and polymerized using a radical initiator to initiate polymerization by the action of either heat or radiation. The device material is preferably polymerized in de-gassed polypropylene molds under nitrogen or in glass molds.

Suitable polymerization initiators include thermal initiators and photoinitiators. Preferred thermal initiators include peroxy free-radical initiators, such as t-butyl(peroxy-2-ethyl) hexanoate and di-(tert-butylcyclohexyl) peroxydicarbonate (commercially available as Perkadox® 16 from Akzo Chemicals Inc., Chicago, Ill.). Particularly in cases where the materials of the present invention do not contain a blue-light absorbing chromophore, preferred photoinitiators include benzoylphosphine oxide initiators, such as 2,4,6-trimethyl-benzoyldiphenyl-phosphine oxide, commercially available as Lucirin® TPO from BASF Corporation (Charlotte, N.C.). Initiators are typically present in an amount equal to about 5% or less of the total formulation weight, and more preferably less than 2% of the total formulation. As is customary for purposes of calculating component amounts, the initiator weight is not included in the formulation weight % calculation.

The particular combination of the ingredients described above and the identity and amount of any additional components are determined by the desired properties of the finished device material. In a preferred embodiment, the device materials of the present invention are used to make IOLs having an optic diameter of 5.5 or 6 mm that are designed to be compressed or stretched and inserted through surgical incision sizes of 2 mm or less. For example, the monomer [3] is combined with at least one mono-functional acrylate or methacrylate monomer [1] and a multifunctional acrylate or methacrylate cross-linker [2] and copolymerized using a radical initiator in a suitable lens mold.

The device material preferably has a refractive index in the hydrated state of at least about 1.50, and more preferably at least about 1.53, as measured by an Abbe' refractometer at 589 nm (Na light source) and 25° C. Optics made from materials having a refractive index lower than 1.50 are necessarily thicker than optics of the same power which are made from materials having a higher refractive index. As such, IOL optics made from materials with comparable mechanical properties and a refractive index lower than about 1.50 generally require relatively larger incisions for IOL implantation.

The proportions of the monomers to be included in the copolymers of the present invention should be chosen so that the copolymer has a glass transition temperature ($T_g$) not greater than about 37° C., which is normal human body temperature. Copolymers having glass transition temperatures higher than 37° C. are not suitable for use in foldable IOLs; such lenses could only be rolled or folded at temperatures above 37° C. and would not unroll or unfold at normal body temperature. It is preferred to use copolymers having a glass transition temperature somewhat below normal body temperature and no greater than normal room temperature, e.g., about 20-25° C., in order that IOLs made of such copolymers can be rolled or folded conveniently at room temperature. $T_g$ is measured by differential scanning calorimetry at 10° C./min., and is determined at the midpoint of the transition of the heat flux curve.

For IOLs and other applications, the materials of the present invention must exhibit sufficient strength to allow devices made of them to be folded or manipulated without fracturing. Thus the copolymers of the present invention will have an elongation of at least 80%, preferably at least 100%, and most preferably between 110 and 200%. This property indicates that lenses made of such materials generally will not crack, tear or split when folded. Elongation of polymer samples is determined on dumbbell shaped tension test specimens with a 20 mm total length, length in the grip area of 4.88 mm, overall width of 2.49 mm, 0.833 mm width of the narrow section, a fillet radius of 8.83 mm, and a thickness of 0.9 mm.

Testing is performed on samples at ambient conditions using an Instron Material Tester (Model No. 4442 or equivalent) with a 50 Newton load cell. The grip distance is set at 14 mm and a crosshead speed is set at 500 mm/minute and the sample is pulled until failure. The elongation (strain) is reported as a fraction of the displacement at failure to the original grip distance. Since the materials to be tested are essentially soft elastomers, loading them into the Instron machine tends to make them buckle. To remove the slack in the material sample a pre-load is placed upon the sample. This helps to reduce the slack and provide a more consistent reading. Once the sample is pre-loaded to a desired value (typically 0.03 to 0.05 N) the strain is set to zero and the test begun. The modulus is calculated as the instantaneous slope of the stress-strain curve at 0% strain ("Young's modulus"), 25% strain ("25% modulus") and 100% strain ("100% modulus").

IOLs made of the ophthalmic device materials of the present invention are more resistant to glistenings than other materials. Glistenings are measured according to the following test. The presence of glistenings is measured by placement of a lens or disk sample into a vial or sealed glass chamber and adding deionized water or a balanced salt solution. The vial or glass chamber is then placed into a water bath preheated to 41° C. Samples are to be maintained in the bath for a minimum of 16 hours and preferably 24±2 hours. The vial or glass chamber is then immediately placed in a water bath preheated to 35° C. and allowed to equilibrate at 35° C. for a minimum of 30 minutes and preferably 30 to 60 minutes. The sample is inspected visually in various on angle or off angle lighting to evaluate clarity while at 35° C. Visualization of glistenings is carried out at 35° C. with light microscopy using a magnification of 50 to 200×. A sample is judged to have many glistenings if, at 50-200× magnification, there are approximately 50 to 100% as many glistenings as observed in control samples based on 65 weight % PEA, 30 weight % PEMA, 3.2 weight % BDDA, and 1.8 weight % OMTP. Similarly, a sample is judged to have few glistenings if there are approximately 10% or more glistenings relative to the quantity observed in control samples. A sample is judged to have very few glistenings if there are approximately 1% or more glistenings relative to a control sample. A sample is judged to be free of glistenings if the number of glistenings detected in the eyepiece is zero. A sample is judged to be substantially free of glistenings if the number of glistenings detected in the eyepiece is less than about $2/mm^3$. It is often very difficult to detect glistenings, especially at surfaces and edges where more defects and debris have formed, so the sample is rastered throughout the entire volume of the lens, varying the magnification levels (50-200×), the aperture iris diaphragm, and the field conditions (using both bright field and dark field conditions) in an attempt to detect the presence of glistenings.

The copolymers of the present invention preferably have an equilibrium water content (EWC) of 0.5 to 3 weight %. EWC is measured by placing one rectangular 0.9×10×20 mm slab in a 20 ml scintillation vial filled with deionized water and subsequently heating in a 35+ C. water bath for a minimum of 20 hours and preferably 48±8 hours. The slab is blotted dry with lens paper and the % water content is calculated as follows:

$$\% \text{ water content} = \frac{(\text{wet weight} - \text{dry weight})}{\text{wet weight}} \times 100$$

IOLs constructed of the device materials of the present invention can be of any design capable of being stretched or compressed into a small cross section that can fit through a 2-mm incision. For example, the IOLs can be of what is known as a one-piece or multi-piece design, and comprise optic and haptic components. The optic is that portion which serves as the lens and the haptics are attached to the optic and are like arms that hold the optic in its proper place in the eye. The optic and haptic(s) can be of the same or different material. A multi-piece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use as other ophthalmic or otorhinolaryngological devices such as contact lenses, keratoprostheses, corneal inlays or rings, otological ventilation tubes and nasal implants.

The invention will be further illustrated by the following examples, which are intended to be illustrative, but not limiting.

The following abbreviations are used throughout the Examples and have the following meanings.

| | |
|---|---|
| PEA | 2-phenylethyl acrylate |
| PEMA | 2-phenylethyl methacrylate |
| BzMA | benzyl methacrylate |
| BDDA | 1,4-butanediol diacrylate |
| IEMA | 2-isocyanatoethyl methacrylate |
| THF | tetrahydrofuran |
| AIBN | azobisisobutyronitrile |
| OMTP | 2-(2H-benzo[d][1,2,3]triazol-2-yl)-4-methyl-6-(2-methylallyl)phenol |
| TMI | 3-isopropenyl-alpha,alpha-dimethylbenzyl isocyanate |
| MEHQ | methyl hydroquinone or 4-methoxyphenol |
| TergNP4-MA | Reacted adduct of Tergitol ™ NP-4 surfactant and methacrylic anhydride or methacryloyl chloride or IEMA |
| TergNP6-MA | Reacted adduct of Tergitol ™ NP-6 surfactant and methacrylic anhydride or methacryloyl chloride or IEMA |
| TergNP9-MA | Reacted adduct of Tergitol ™ NP-9 surfactant and methacrylic anhydride or methacryloyl chloride or IEMA |
| TergNP11-MA | Reacted adduct of Tergitol ™ NP-11 surfactant and methacrylic anhydride or methacryloyl chloride or IEMA |
| TergNP15-MA | Reacted adduct of Tergitol ™ NP-15 surfactant and methacrylic anhydride or methacryloyl chloride or IEMA |
| TergNP40-MA | Reacted adduct of Tergitol ™ NP-40 surfactant and methacrylic anhydride |
| TergNP4-TMI | Reacted adduct of Tergitol ™ NP-4 surfactant and TMI |
| TergNP6-TMI | Reacted adduct of Tergitol ™ NP-6 surfactant and TMI |
| TergNP9-TMI | Reacted adduct of Tergitol ™ NP-9 surfactant and TMI |
| TergNP11-TMI | Reacted adduct of Tergitol ™ NP-11 surfactant and TMI |
| TergNP15-TMI | Reacted adduct of Tergitol ™ NP-15 surfactant and TMI |
| TritX15-MA | Reacted adduct of Triton ™ X-15 surfactant and methacrylic anhydride or methacryloyl chloride or IEMA |
| TritX35-MA | Reacted adduct of Triton ™ X-35 surfactant and methacrylic anhydride or methacryloyl chloride or IEMA |
| TritX114-MA | Reacted adduct of Triton ™ X-114 surfactant and methacrylic anhydride or methacryloyl chloride or IEMA |
| TritX102-MA | Reacted adduct of Triton ™ X-102 surfactant and methacrylic anhydride or methacryloyl chloride or IEMA |

EXAMPLE 1

TritonX15-MA. 51.2 g (176 mmol based on equivalent weight=291) of Triton™ X-15 (Dow/Union Carbide) and 20 mg MEHQ (Aldrich, Milwaukee, Wis.) were dissolved in 300 ml anhydrous THF (Aldrich) in a 1 liter round bottom flask equipped with magnetic stirrer and nitrogen inlet. 27.6 g (178 mmol) of 2-isocyanatoethyl methacrylate (IEMA) (Aldrich) and 20 mg stannous octoate (Aldrich) were added and the reaction mixture was heated to 60° C. for 20 hours. The solvent was removed via rotary evaporation and the resulting liquid was further dried under vacuum (~0.1 mm Hg) for 40 hours.

EXAMPLE 2

TritX35-MA. The reaction was carried out as in Example 1 using 53.6 g (169 mmol based on equivalent weight=317) of Triton™ X-35 (Dow/Union Carbide) and 20 mg MEHQ (Aldrich, Milwaukee, Wis.) and 24.3 g (157 mmol) of 2-isocyanatoethyl methacrylate (IEMA) (Aldrich) resulting in a liquid which was further dried under vacuum (~0.1 mm Hg) for 40 hours.

EXAMPLE 3

TritX102-MA. The reaction was carried out as in Example 1 using 49.5 g (66.9 mmol based on equivalent weight=740) of Triton™ X-102 (Dow/Union Carbide) and 11.3 g (72.8 mmol) of 2-isocyanatoethyl methacrylate (IEMA) (Aldrich) resulting in a liquid which was further dried under vacuum (~0.1 mm Hg) for 40 hours.

EXAMPLE 4

TritX114-MA. The reaction was carried out as in Example 1 using 51.5 g (96.3 mmol based on equivalent weight=535) of Triton™ X-114 (Dow/Union Carbide) and 17.1 g (110.2) of 2-isocyanatoethyl methacrylate (IEMA) (Aldrich) resulting in a liquid which was further dried under vacuum (~0.1 mm Hg) for 40 hours.

EXAMPLE 5

TergNP4-MA. The reaction was carried out as in Example 1 using 49.7 g (117 mmol based on equivalent weight=424) of Tergitol™ NP-4 (Dow/Union Carbide) and 19.4 g (125 mmol) of 2-isocyanatoethyl methacrylate (IEMA) (Aldrich) resulting in a liquid which was further dried under vacuum (~0.1 mm Hg) for 40 hours.

EXAMPLE 6

TergNP11-MA. The reaction was carried out as in Example 1 using 51.2 g (70.6 mmol based on equivalent weight=725) of Tergitol™ NP-11 (Dow/Union Carbide) and 16.1 g (104 mmol) of 2-isocyanatoethyl methacrylate (IEMA) (Aldrich) resulting in a liquid which was further dried under vacuum (~0.1 mm Hg) for 40 hours.

EXAMPLE 7

TergNP15-MA. The reaction was carried out as in Example 1 using 50.9 g (55.0 mmol based on equivalent weight=926) of Tergitol™ NP-15 (Dow/Union Carbide) and 9.72 g (62.6 mmol) of 2-isocyanatoethyl methacrylate (IEMA) (Aldrich) resulting in a viscous liquid which was further dried under vacuum (~0.1 mm Hg) for 40 hours.

EXAMPLE 8

TergNP40-MA. 76.7 g (38.7 mmol based on equivalent weight=1983) of Tergitol NP-40 (Dow/Union Carbide) was dissolved in 176 g anhydrous pyridine. 20 mg MEHQ and 50 mg dibutyltin dilaurate (Aldrich) were added followed by 12.4 g methacrylic anhydride (Alfa Aesar, 94%). The reaction mixture was heated at 50° C. for 20 hours and the solid isolated by precipitation in cold diethyl ether 3 times to give 56 g (71%) of a white solid which was dried under vacuum (~0.1 mm Hg) for 72 hours.

EXAMPLE 9

TergNP4-TMI. 5.11 g (12.1 mmol) of Tergitol™ NP-4 and 10 mg MEHQ (Aldrich, Milwaukee, Wis.) were dissolved in 100 ml anhydrous THF (Aldrich) in a 250 ml round bottom flask equipped with magnetic stirrer and nitrogen inlet. 2.54 g (12.6 mmol) of 3-isopropenyl-alpha,alpha-dimethylbenzyl isocyanate (TMI) (Aldrich) and 10 mg dibutyltin dilaurate (Aldrich) were added and the reaction mixture was heated to 60° C. for 20 hours under a nitrogen blanket. The solvent was removed via rotary evaporation and the resulting liquid was further dried under vacuum (~0.1 mm Hg) for 20 hours.

EXAMPLE 10

TergNP6-TMI. The reaction was carried out as in Example 9 using 5.00 g (9.84 mmol) of Tergitol™ NP-6 and 2.28 g (1.14 mmol) of TMI resulting in a liquid which was further dried under vacuum (~0.1 mm Hg) for 20 hours.

EXAMPLE 11

TergNP9-TMI. The reaction was carried out as in Example 9 using 5.16 g (7.84 mmol) of Tergitol™ NP-9 and 1.70 g (8.29 mmol) of TMI resulting in a liquid which was further dried under vacuum (~0.1 mm Hg) for 20 hours.

EXAMPLE 12

TergNP15-TMI. The reaction was carried out as in Example 9 using 4.56 g (4.92 mmol) of Tergitol™ NP-15 and 1.00 g (4.98 mmol) of TMI 5 resulting in a liquid which was further dried under vacuum (~0.1 mm Hg) for 20 hours.

The refractive index values and molecular weights of the starting alkyllphenol ethoxylate alcohols were measured prior to functionalizing with reactive groups as shown in Table 1. Refractive index values were measured at 35° C. GPC number average molecular weights were measured in THF relative to polystyrene standards. Number average molecular weight values were also estimated using a Bruker 400 MHz NMR spectrometer using $CD_2Cl_2$ as solvent. Equivalent weights were determined using a modified hydroxyl number (OH#) test method in which 2-3 grams of alkylphenol ethoxylate were treated with acetic anhydride in pyridine to give a mixture of the alkylphenol ethoxylate acetate and acetic acid. The mixture was then titrated with a solution of 1.0 N potassium hydroxide to a basic endpoint using phenolphthalein indicator. A blank containing acetic anhydride and pyridine was also titrated and the equivalence points of sample and blank were used to calculate the hydroxyl number (OH#=mg KOH/g sample) and corresponding equivalent weight using the following equation: Equivalent Weight=56,100/OH#.

TABLE 1

| Alkylphenol Ethoxylate | Average Number Of Ethylene Oxide Units | R.I | Mn (GPC) | Mn ($^1$H NMR) | Equivalent Weight (from OH#) |
|---|---|---|---|---|---|
| Triton ™ X-15 | 1.5 | 1.506 | 279 | 282 | 291 |
| Triton ™ X-35 | 3 | 1.502 | 330 | 317 | 317 |
| Triton ™ X-114 | 7.5 | 1.502 | 632 | 555 | 535 |
| Triton ™ X-102 | 12 | 1.484 | 891 | 729 | 740 |
| Tergitol ™ NP-4 | 4 | 1.495 | 456 | 404 | 424 |
| Tergitol ™ NP-6 | 6 | 1.490 | 576 | 497 | 508 |

TABLE 1-continued

| Alkylphenol Ethoxylate | Average Number Of Ethylene Oxide Units | R.I | Mn (GPC) | Mn ($^1$H NMR) | Equivalent Weight (from OH#) |
|---|---|---|---|---|---|
| Tergitol ™ NP-9 | 9 | 1.485 | 795 | 645 | 658 |
| Tergitol ™ NP-11 | 11 | 1.484 | 870 | 689 | 725 |
| Tergitol ™ NP-15 | 15 | 1.482 | 1100 | 843 | 926 |
| Tergitol ™ NP-40 | 40 | — | — | — | 1983 |

EXAMPLE 13

Lens Materials

The reaction components listed in Tables 2-4, except for AIBN, were mixed together with stirring or shaking for at least 30 minutes at 23° C., until all components were dissolved. The AIBN was subsequently added and the reaction mixture was stirred for a minimum of 5 minutes, until the initiator was dissolved. The reactive components are reported in grams.

The reactive components were purged for approximately 15 minutes using N$_2$ and placed inside a low humidity N$_2$ purged glove box.

The reactive components were syringed or pipetted onto clean polypropylene mold halves containing 1×10×20 mm rectangular wells and then covered with the complementary flat polypropylene mold halves. The mold halves were compressed using binder clips and the mixtures were cured at 70° C. for 16 hours using a Yamato DKN400 constant temperature oven. The molds were allowed to cool to room temperature. The top mold halves were removed and the rectangular polymer slabs were removed from the wells with tweezers and placed individually in 38×8 mm Histo Plas tissue processing capsules (Bio Plas Inc., San Rafael, Calif.). The slabs were extracted in acetone for a minimum of 16 hours and then air dried at ambient temperature for 20 hours, followed by high vacuum (~0.1 mm Hg) at ambient temperature for 20 hours, and high vacuum at 70° C. for 20 hours.

TABLE 2

| | Example % (w/w) | | | |
|---|---|---|---|---|
| Component | 13A | 13B | 13C | 13D |
| Ex 1 | 0 | 0 | 0 | 15.0 |
| Ex 2 | 0 | 0 | 14.8 | 0 |
| Ex 3 | 11.9 | 0 | 0 | 0 |
| Ex 4 | 0 | 12.4 | 0 | 0 |
| PEA | 57.0 | 56.7 | 55.1 | 55.1 |
| PEMA | 26.8 | 26.6 | 26.0 | 25.4 |
| BDDA | 2.7 | 2.7 | 2.7 | 3.0 |
| OMTP | 1.5 | 1.5 | 1.5 | 1.5 |
| AIBN | 0.45 | 0.46 | 0.45 | 0.45 |

TABLE 3

| | Example % (w/w) | | | | | |
|---|---|---|---|---|---|---|
| Component | 13E | 13F | 13G | 13H | 13I | 13J |
| Ex 5 | 13.1 | 0 | 0 | 0 | 0 | 0 |
| Ex 6 | 0 | 12.1 | 0 | 0 | 0 | 0 |
| Ex 7 | 0 | 0 | 11.6 | 0 | 0 | 0 |
| Ex 9 | 0 | 0 | 0 | 14.3 | 0 | 0 |
| Ex 10 | 0 | 0 | 0 | 0 | 13.4 | 0 |
| Ex 11 | 0 | 0 | 0 | 0 | 0 | 12.9 |
| PEA | 56.3 | 56.9 | 57.3 | 55.5 | 56.0 | 56.4 |
| PEMA | 26.0 | 26.3 | 26.4 | 25.7 | 25.9 | 26.1 |
| BDDA | 3.1 | 3.1 | 3.1 | 3.0 | 3.1 | 3.1 |
| OMTP | 1.6 | 1.6 | 1.6 | 1.5 | 1.6 | 1.6 |
| AIBN | 0.48 | 0.45 | 0.45 | 0.40 | 0.44 | 0.44 |

TABLE 4

| | Example % (w/w) | | | | | |
|---|---|---|---|---|---|---|
| Component | 13K | 13L | 13M | 13N | 13O | 13P |
| Ex 8 | 0 | 0 | 0 | 0 | 6.1 | 5.9 |
| Ex 12 | 9.8 | 7.4 | 4.9 | 2.6 | 0 | 0 |
| PEA | 58.7 | 60.3 | 61.9 | 63.3 | 48.1 | 63.1 |
| PEMA | 27.0 | 27.8 | 28.5 | 29.3 | 43.8 | 7.3 |
| BzMA | 0 | 0 | 0 | 0 | 0 | 21.7 |
| BDDA | 2.81 | 2.9 | 3.0 | 3.0 | 1.9 | 2.0 |
| OMTP | 1.6 | 1.7 | 1.7 | 1.8 | 0 | 0 |
| AIBN | 0.58 | 0.59 | 0.63 | 0.52 | 0.53 | 0.55 |

The % extractables were calculated as follows:

$$\% \text{ extractables} = \frac{(\text{non-extracted weight} - \text{extracted weight})}{\text{non-extracted weight}} \times 100$$

The equilibrium water content (EWC) was measured by placing one slab in a 20 ml scintillation vial filled with deionized water and subsequently heating in a 35° C. water bath for a minimum of 20 hours. The slab was blotted dry with lens paper and the % water content was calculated as follows:

$$\% \text{ water content} = \frac{(\text{wet weight} - \text{dry weight})}{\text{wet weight}} \times 100$$

The refractive index values of hydrated samples were measured using a Bausch & Lomb refractometer (catalog #33.46.10) at 35° C.

The extent of glistening formation was evaluated by carrying out a 41° to 35° C. change in temperature (ΔT) test. In brief, samples were first placed in 20 ml scintillation vials containing deionized water and heated at 41° C. for a minimum of 20 hours. The entire cross section (~200 mm$^2$) of samples was examined for glistening formation approximately 30 to 60 minutes after cooling to ambient temperature using an Olympus BX60 microscope equipped with a 10× objective. The number of glistening was counted visually at 3 different points along the slab, typically in the center and approximately 2, 5, and 7 mm from the left edge. The samples were also visually inspected for haze after the ΔT test.

The refractive index (R.I.), % extractables, appearance of haze, and glistening results are shown in Table 5.

TABLE 5

| Ex. # | R.I. | % Extractables | Clarity (during glistening test) | Relative glistening formation |
|---|---|---|---|---|
| 13A | 1.546 | 6.2 | clear | many |
| 13B | 1.545 | 5.9 | haze | many |
| 13C | 1.546 | 7.0 | haze | many |
| 13D | 1.548 | 3.5 | haze | many |
| 13E | 1.546 | 3.6 | clear | many |
| 13F | 1.546 | 3.7 | clear | few |
| 13G | 1.545 | 4.8 | clear | many |
| 13H | 1.546 | 3.9 | clear | many |
| 13I | 1.543 | 6.2 | clear | few |
| 13J | 1.544 | 4.9 | clear | very few |
| 13K | 1.551 | 3.8 | clear | very few |
| 13L | 1.550 | 3.5 | clear | very few |
| 13M | 1.550 | 2.8 | clear | very few |
| 13N | 1.550 | 2.0 | clear | very few |
| 13O | 1.548 | 1.9 | clear | 0 |
| 13P | 1.545 | 2.1 | clear | 0 |

The results of Examples 13A through 13P show that the reaction mixture components and their amounts may be varied. All materials were clear and showed low haze prior to contact with water. Examples 13B through 13D showed noticeable haze after equilibrating in deionized water at 41° C. followed by cooling to 35° C.

The refractive index values were generally high, between 1.54 and 1.55 for all examples.

The equilibrium water contents (EWCs) at 35° C. were less than 1.0% for Examples 13A through 13N, which contained functionalized alkylphenol ethoxylates with between 1 and 15 ethylene oxide repeat units. EWC values of 1.5% were observed for Examples 13O and 13P, which contained functionalized alkylphenol ethoxylates with an average of 40 ethylene oxide repeat units.

In general, fewer glistenings were observed when higher molecular weight alkylphenol ethoxylates were used. The ethylene oxide content of select nonylphenol ethoxylates are shown in Table 6 Further, increased loadings of the lower molecular weight functionalized alkylphenol ethoxylates of up to 20 weight % also reduced or completely eliminated glistening formation.

TABLE 6

| Alkylphenol ethoxylate | Molecular Weight (Mn) | Ethylene Oxide Wt. % | <sup>a</sup>Glistening Formation |
|---|---|---|---|
| Tergitol ™ NP-4 | 424 | 52 | High |
| Tergitol ™ NP-6 | 508 | 60 | High |
| Tergitol ™ NP-9 | 658 | 69 | Medium |
| Tergitol ™ NP-11 | 725 | 72 | Medium |
| Tergitol ™ NP-15 | 926 | 78 | Low |
| Tergitol ™ NP-40 | 1983 | 89 | 0 |

<sup>a</sup>Typical loading of 5-10 weight %

The materials from Examples 13O and 13P, which showed zero glistenings under the conditions studied, were analyzed to determine their tensile properties. The results are shown in Table 7, below.

TABLE 7

| Ex. # | Stress at Break (MPa) | Strain at Break (%) | Young's Modulus (MPa) | 25% Secant Modulus (MPa) | 100% Secant Modulus (MPa) |
|---|---|---|---|---|---|
| 13O | 8.7 | 140 | 46.5 | 9.3 | 4.8 |
| 13P | 7.1 | 145 | 20 | 4.6 | 3.1 |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. An ophthalmic or otorhinolaryngological device selected from the group consisting of intraocular lenses; contact lenses; keratoprostheses; corneal inlays or rings; otological ventilation tubes; and nasal implants, wherein the device comprises a copolymeric ophthalmic or otorhinolaryngological device material formed by polymerizing a composition comprising a) 75 to 97% (w/w) of a monofunctional acrylate or methacrylate monomer of formula [1]:

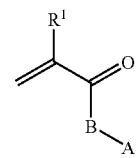

[1]

wherein
B=$O(CH_2)_n$, $NH(CH_2)_n$, or $NCH_3(CH_2)_n$;
$R^1$=H, $CH_3$, $CH_2CH_3$, or $CH_2OH$;
n=0-12;
A=$C_6H_5$ or $O(CH_2)_mC_6H_5$, where the $C_6H_5$ group is optionally substituted with —$(CH_2)_nH$, —$O(CH_2)H$, —$CH(CH_3)_2$, —$C_6H_5$, —$OC_6H_5$, —$CH_2C_6H_5$, F, Cl, Br, or I; and
m=0-22;

b) a difunctional acrylate or methacrylate cross-linking monomer of formula [2]:

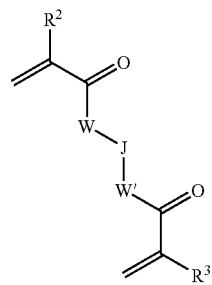

[2]

wherein
$R^2$, $R^3$ independently=H, $CH_3$, $CH_2CH_3$, or $CH_2OH$;
W, W' independently=$O(CH_2)_d$, $NH(CH_2)_d$, $NCH_3(CH_2)_d$, $O(CH_2)_dC_6H_4$, $O(CH_2CH_2O)_dCH_2$, $O(CH_2CH_2CH_2O)_dCH_2$, $O(CH_2CH_2CH_2CH_2O)_dCH_2$, or nothing;
J=$(CH_2)_a$, $O(CH_2CH_2O)_b$, O, or nothing, provided that if W and W'=nothing, then J≠nothing;
d=0-12;
a=1-12; and
b=1-24;

and
c) 3% (w/w) of an alkylphenol ethoxylate monomer of formula [3]:

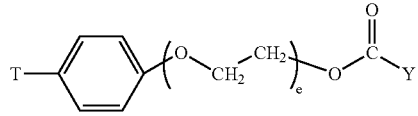

wherein:
T=$C_8H_{17}$ or $C_9H_{19}$;
e=40;

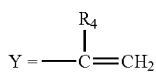

or
$R^4$=H, $CH_3$ and $CH_2CH_3$
provided that the device material has a glass transition temperature not greater than 25° C.

2. The device of claim 1 wherein
B=$O(CH_2)_n$;
$R^1$=H or $CH_3$;
n=1-4; and
A=$C_6H_5$.

3. The device of claim 1 wherein
$R^2$, $R^3$ independently=H or $CH_3$;
W, W' independently=$O(CH_2)_d$, $O(CH_2)_dC_6H_4$, or nothing;
J=$O(CH_2CH_2O)_b$ or nothing, provided that if W and W'=nothing, then J≠nothing;
d=0-6; and
b=1-10.

4. The device of claim 1 wherein:
$R^4$=H or $CH_3$.

5. The device of claim 4 wherein:
T=2,4,4-trimethylpentan-2-yl alkyl or 3-ethyl-4-methylhexan-2-yl alkyl;

and

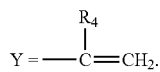

6. The device of claim 1 wherein the monomer of formula [1] is selected from the group consisting of benzyl methacrylate; 2-phenylethyl methacrylate; 3-phenylpropyl methacrylate; 4-phenylbutyl methacrylate; 5-phenylpentyl methacrylate; 2-phenoxyethyl methacrylate; 2-(2-phenoxyethoxy) ethyl methacrylate; 2-benzyloxyethyl methacrylate; 2-(2-(benzyloxy)ethoxy)ethyl methacrylate; 3-benzyloxypropyl methacrylate; benzyl acrylate; 2-phenylethyl acrylate; 3-phenylpropyl acrylate; 4-phenylbutyl acrylate; 5-phenylpentyl acrylate; 2-phenoxyethyl acrylate; 2-(2-phenoxyethoxy) ethyl acrylate; 2-benzyloxyethyl acrylate; 2-(2-(benzyloxy) ethoxy)ethyl acrylate; and 3-benzyloxypropyl acrylate.

7. The device of claim 1 wherein the monomer of formula [2] is selected from the group consisting of ethylene glycol dimethacrylate; diethylene glycol dimethacrylate; triethylene glycol dimethacrylate; 1,6-hexanediol dimethacrylate; 1,4-butanediol dimethacrylate; 1,4-benzenedimethanol dimethacrylate; ethylene glycol diacrylate; diethylene glycol diacrylate; triethylene glycol diacrylate; 1,6-hexanediol diacrylate; 1,4-butanediol diacrylate; and 1,4-benzenedimethanol diacrylate.

8. The device of claim 1 wherein the amount of monomer [1] is 80 to 95% (w/w).

9. The device of claim 1 wherein the amount of monomer [2] is 0.5 to 3% (w/w).

10. The device of claim 1 further comprising an ingredient selected from the group consisting of a polymerizable UV absorber and a polymerizable colorant.

11. The device of claim 10 comprising 0.1-5% (w/w) of a polymerizable UV absorber and 0.01-0.5% (w/w) of a polymerizable colorant.

12. The device of claim 1 wherein the device is an intraocular lens.

* * * * *